United States Patent [19]

Simpson

[11] Patent Number: 4,661,094
[45] Date of Patent: Apr. 28, 1987

[54] PERFUSION CATHETER AND METHOD

[75] Inventor: John B. Simpson, Woodside, Calif.

[73] Assignee: Advanced Cardiovascular Systems, Mountain View, Calif.

[21] Appl. No.: 730,680

[22] Filed: May 3, 1985

[51] Int. Cl.⁴ .............................................. A61F 2/66
[52] U.S. Cl. ...................................... 604/53; 604/164; 604/280
[58] Field of Search ................... 604/8, 164, 165, 266, 604/272, 280, 44, 283, 284, 264, 28, 49, 53; 128/657, 772

[56] References Cited

U.S. PATENT DOCUMENTS

| | | | |
|---|---|---|---|
| 3,633,585 | 1/1972 | McDonald, Jr. | 604/8 |
| 3,828,767 | 8/1974 | Spiroff | 128/658 |
| 3,960,153 | 6/1976 | Carey et al. | 604/164 |
| 4,280,500 | 7/1981 | Ono | 128/348 |
| 4,318,402 | 3/1982 | Vaillancourt | 128/214 |
| 4,464,176 | 8/1984 | Wijayarathna | 604/164 |
| 4,493,696 | 1/1985 | Uldall | 604/43 |
| 4,540,404 | 9/1985 | Wolvek | 604/96 |
| 4,545,390 | 10/1985 | Leary | 128/772 |
| 4,571,240 | 2/1986 | Samson et al. | 604/96 |
| 4,573,470 | 3/1986 | Samson et al. | 128/344 |

OTHER PUBLICATIONS

USCI Catalogue 1974/5070107.

Primary Examiner—Stephen C. Pellegrino
Assistant Examiner—John D. Ferros
Attorney, Agent, or Firm—Flehr, Hohbach, Test, Albritton & Herbert

[57] ABSTRACT

Perfusion catheter adapted to be positioned in at least a partially occluded blood vessel having a lesion or restriction therein comprising an elongate flexible plastic tubular member having a flow passage extending therethrough. The member has proximal and distal ends and a fitting carried by the proximal end. The member has a plurality of holes spaced apart longitudinally from the distal end and permitting the flow of liquid from and into the flow passage through the holes when the catheter is positioned in the lesion or restriction so that at least some of the holes are on one side of the lesion or restriction and other holes are on the other side of the lesion or restriction.

2 Claims, 3 Drawing Figures

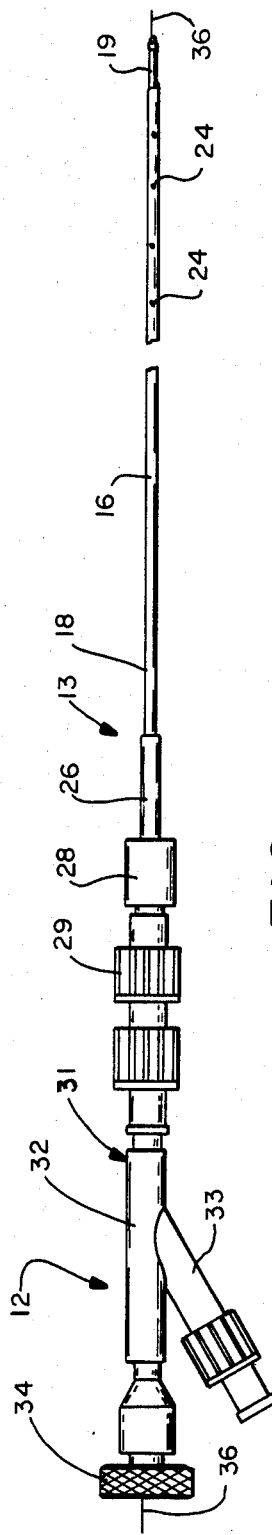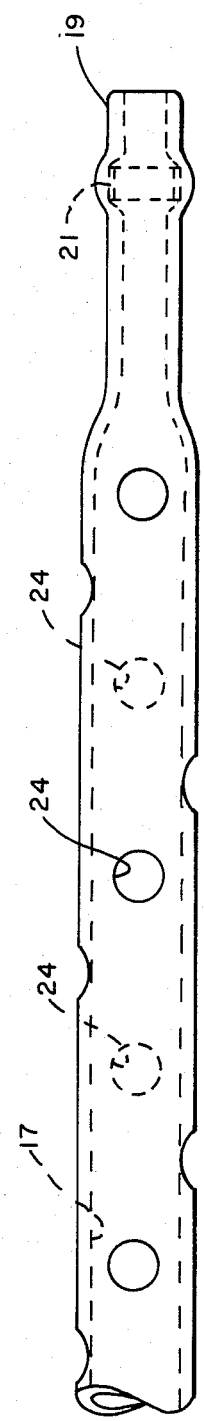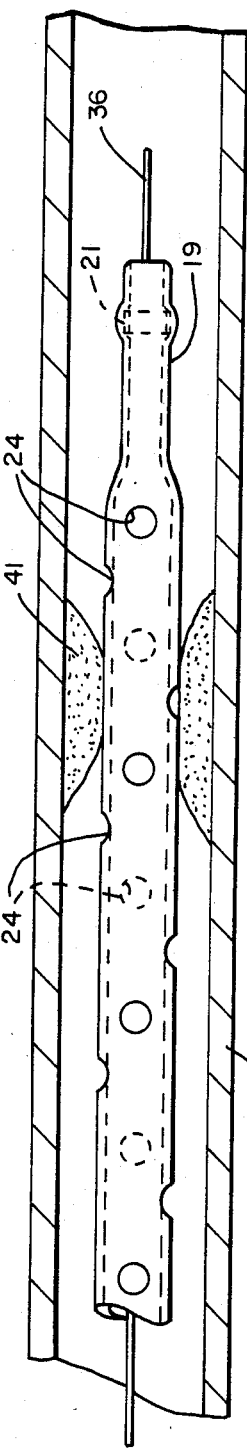

PERFUSION CATHETER AND METHOD

This invention relates to perfusion catheters and methods and more particularly those which are utilized for bypasses during cardiovascular procedures.

During cardiovascular procedures and, in particular, ones utilizing angioplasty, there have been occurrences in which plaque has become at least partially dislodged and moved to block an arterial passage. There is a need for a device which will continue to permit the passage of blood past the plaque so as to prevent any substantial damage to the heart muscle. There also is a need for such a device during bypass operations.

In general, it is an object of the present invention to provide a perfusion catheter and method which can be utilized in cardiovascular procedures and particularly for bypasses.

Another object of the invention is to provide a perfusion catheter of the above type which is relatively easy to fabricate.

Additional objects and features of the invention will appear from the following description in conjunction with the accompanying drawing.

FIG. 1 is a side elevational view of a perfusion catheter incorporating the present invention.

FIG. 2 is an enlarged view of the distal extremity of the perfusion catheter shown in FIG. 1.

FIG. 3 is a cross sectional view showing the manner in which the perfusion catheter is utilized in bypassing plaque in a vessel.

In general the perfusion catheter of the present invention is adapted to be positioned in at least a partially occluded blood vessel having a restriction formed therein. It consists of an elongate flexible plastic tubular element having a flow passage extending therethrough. The element has proximal and distal ends. A fitting is carried by the proximal end. The element has a plurality of holes spaced apart longitudinally from the distal extremity of the element. They are spaced along a sufficient distance of the element so that when the perfusion catheter is disposed in a vessel and having the distal extremity disposed on one side of a restriction in the vessel and another portion of the element disposed on another side of the restriction, blood can flow through at least one of the holes on one side of the restriction through the flow passage in the catheter and out through another of the holes on the other side of the restriction whereby blood can flow through the perfusion catheter even though there is a restriction in the blood vessel.

More in particular, the perfusion catheter 11 consists of a fitting assembly 12 and a tubular assembly 13. The tubular assembly 13 consists of an elongate flexible tubular member 16 formed of a suitable plastic material such as polyethylene tubing which has been irradiated to provide what is typically called shrink tubing. The tubing can have any suitable length as, for example, 135 centimeters. Depending upon the application, the length of the tubing and the diameter can vary. Typically the outside diameter can range from 0.040 to 0.070 inches and by way of example a perfusion catheter 11 suitable for use in human blood vessels can have an outside diameter of 0.058 inches and an inside diameter of 0.041 inches. The tubular member 16 has a flow passage extending therethrough. The tubular member has proximal and distal ends 18 and 19. The distal extremity of the tubular member 16 is necked down over a radiopaque metallic band 21. By way of example, the metallic band 21 can be formed of gold. The band 21 can have an outside diameter of 0.034 inches and an inside diameter of 0.030 inches and thus can have a wall thickness of 0.002 inches and a width of 0.023 inches.

The tubular member 16 when shrunk down onto the ring 21 has an outside dimension overlying the ring of approximately 0.04 inches. The ring 21 can be positioned a suitable distance from the distal extremity of the tubular member as, for example, 2 to 3 millimeters. The passage 17 at the distal extremity of the tubular member can have a suitable dimension such as 0.028 of an inch and the tubular member an outside diameter of 0.0415 inches. A plurality of holes 24 are provided in the tubular member 16. The holes 24 are spaced apart longitudinally of the tubular member and are also spaced circumferentially of the tubular member. The holes 24 are positioned so that they start near the distal extremity 19 of the catheter and extend inwardly toward the proximal extremity of the catheter for a suitable distance as, for example, 11 or 12 centimeters. The holes can have a suitable diameter as, for example, 0.020 to 0.025 of an inch and preferably a diameter of 0.023 inches. The holes can be spaced apart a suitable distance as, for example, from 2.5 to 3.5 millimeters. In general, each successive hole is offset by 90° with respect to the preceding hole. Thus there are provided four rows of holes which are offset by 90° with respect to each other. The holes are positioned so as to form a gradually curved line extending longitudinally of the tubular member 16.

The proximal extremity of the tubular element 16 is disposed within another flexible tubular member 26. The tubular member 26 is seated within a fitting 28 of the fitting assembly 12 and has disposed therein the tubular member 16. The fitting 28 is connected to another fitting 29 and the fitting 29 is connected to a Y adapter 31. The Y adapter 31 is provided with two arms 32 and 33 with the arm 33 being provided with a conventional Luer fitting. The arm 32 is provided with a thumb screw 34 which is adapted to form a tight seal about a conventional guide wire 36 which extends through the fitting assembly 12 and through the tubular member 16. The arm 33 can be used for injection of liquids such as a radiocontrast dye.

Operation and use of the perfusion catheter and its use in the method may now be briefly described in conjunction with FIG. 3. Let it be assumed that an emergency has arisen in that a lesion or restriction 41 has been formed in a blood vessel 42 in a human body and that it is desired to increase the blood flow or to establish a blood flow across the lesion. This is typically accomplished by first introducing a guide wire 36 into the patient and passing it through the lesion. Thereafter, the perfusion catheter 11 can be inserted over the guide wire 36 and introduced through the lesion. The distal extremity 19 is of a substantially reduced diameter which facilitates its passing through the lesion. The position of the distal extremity of the perfusion catheter can be observed under x-rays by the use of conventional fluoroscopy. In utilizing x-rays, the positioning of the ring 21 is observed. Typically, the distal extremity of the perfusion catheter is positioned so that it extends slightly beyond the restriction or lesion 41 so that one or more of the holes 24 are positioned on one side of the lesion and others of the holes 24 are positioned on the other side of the restriction or lesion. As soon as this has been accomplished, blood will begin to flow in its normal direction going into the holes on one side of the restriction, through the flow passage 17 in the perfusion catheter and then passing out through the other holes on the other side of the restriction as shown by the arrows 43 in FIG. 3. If desired, the guide wire 36 can be removed after the perfusion catheter has been placed in a desired position. The perfusion catheter makes it possible to continue the supply of blood into the area where it had been cut off by the restriction 42 as, for example, to the heart muscle. After the perfusion catheter has performed its function and the necessary remedial action has been taken by the doctor, the perfusion catheter can be removed.

From the foregoing, it can be seen that the perfusion catheter can be readily introduced into a vessel and is particularly useful in emergency situations where it is desired to establish immediate blood flow past a restriction or lesion such as the restriction or lesion 41. As soon as the need for the perfusion catheter has been satisfied, the perfusion catheter can be readily removed from the arterial vessel merely by withdrawing the same. If desired, the guide wire can remain in place so that other devices as, for example, a balloon type catheter can be utilized to reduce the size of the flow passage past the lesion 41.

The perfusion catheter is relatively simple in construction and is easily fabricated. It has a very small distal extremity which facilitates its placement through small openings and lesions or restrictions in blood vessels. The use of the radiopaque ring which is retained by the distal extremity makes it possible to visually observe the positioning of the extremity of the perfusion catheter under x-rays.

What is claimed is:

1. In a method for maintaining blood flow across a stenosis in a blood vessel by the use of a perfusion catheter comprised of a flexible tubular member having a flow passage extending longitudinally of the same and having a plurality of spaced apart holes spaced longitudinally from the distal extremity of the tubular member and in communication with the flow passage in the tubular member, the method comprising inserting the perfusion catheter into the blood vessel of the patient so that the perfusion catheter extends through the stenosis so that at least one of the holes in the perfusion catheter is disposed on one side of the stenosis and at least one of the holes is disposed on the other side of the stenosis and at least one of the holes is disposed on the other side of the stenosis so that blood can flow into and out of at least certain of the holes in the tubular member and through the flow passage in the tubular member and across the stenosis to thereby permit blood to continue to flow through the blood vessel and across the stenosis.

2. In a method for maintaining blood flow across a stenosis in a blood vessel by the use of a perfusion catheter comprised of a flexible tubular member having a flow passage extending longitudinally of the same and having a plurality of spaced apart holes spaced longitudinally from the distal extremity of the tubular member and in communication with the flow passage in the tubular member and a guide wire, the method comprising inserting a guide wire into a vessel of the patient so that the distal extremity of the guide wire crosses the stenosis in the blood vessel, and introducing the perfusion catheter into the blood vessel over the guide wire so that the perfusion catheter extends through the stenosis so that at least one of the holes in the perfusion catheter is disposed on one side of the stenosis and at least one of the holes is disposed on the other side of the stenosis so that blood can flow into and out of at least certain of the holes in the tubular member and through the flow passage in the tubular member and across the stenosis to thereby permit blood to continue to flow through the blood vessel and across the stenosis.

* * * * *